United States Patent [19]

Brickl et al.

[11] Patent Number: 4,708,868

[45] Date of Patent: Nov. 24, 1987

[54] ORAL ANTI-DIABETIC PHARMACEUTICAL FORMS AND THE PREPARATION THEREOF

[75] Inventors: Rolf Brickl, Warthausen; Gottfried Schepky, Biberach; Eckhard Rupprecht, Aulendorf-Tannhausen; Andreas Greischel, Biberach, all of Fed. Rep. of Germany

[73] Assignee: Dr. Karl Thomae GmbH, Biberach an der Riss, Fed. Rep. of Germany

[21] Appl. No.: 616,010

[22] Filed: May 31, 1984

[30] Foreign Application Priority Data

Jun. 8, 1983 [DE] Fed. Rep. of Germany ....... 3320583

[51] Int. Cl.$^4$ .................. A61K 31/79; A61K 31/745; A61K 31/495; A61K 31/47

[52] U.S. Cl. ......................................... 924/80; 424/83; 514/255; 514/309; 514/378; 514/412; 514/471; 514/584; 514/861

[58] Field of Search .................... 424/80, 83; 514/255, 514/309, 378, 866, 584, 471, 412; 546/141, 142; 544/406

[56] References Cited

U.S. PATENT DOCUMENTS

| | | | |
|---|---|---|---|
| 3,668,215 | 6/1972 | Plumpe et al. | 548/209 |
| 3,669,966 | 6/1972 | Ambrogi et al. | 544/406 |
| 3,708,486 | 1/1973 | Ruffer et al. | 514/866 |
| 3,883,648 | 5/1975 | Ross et al. | 424/44 |
| 4,430,339 | 2/1984 | Eisteffer et al. | 514/475 |

FOREIGN PATENT DOCUMENTS

| | | |
|---|---|---|
| 0068191 | 1/1983 | European Pat. Off. . |
| 0086468 | 8/1983 | European Pat. Off. . |
| 2355743 | 5/1975 | Fed. Rep. of Germany . |
| 3100535 | 8/1982 | Fed. Rep. of Germany . |
| 3225188 | 1/1984 | Fed. Rep. of Germany . |

Primary Examiner—J. R. Brown
Assistant Examiner—John W. Rollins
Attorney, Agent, or Firm—Weissenberger, Hammond & Littell

[57] ABSTRACT

This invention is directed to novel galenic preparation forms for providing an oral anti-diabetic agent having an improved release of active substance and to processes for producing these preparation forms. The pharmaceutical compositions are characterized in that the onset of the activity and the duration of activity are adapted to the particular needs of diabetics with regard to proper control of metabolism and the associated proper release of insulin. A basic or acidic excipient in a solvent is added to the anti-diabetically active substance in a quantity such that the active substance is made soluble, and then a solubilizing agent is added. The solution is applied to a water-insoluble carrier, the solvent is evaporated, and the residue is further processed to yield the various preparation forms.

16 Claims, 10 Drawing Figures

FIG. 9 COMPARISON OF GLUCOSE LEVELS OF HEALTHY FASTED VOLUNTEERS

COMPARISON OF GLUCOSE LEVELS OF
HEALTHY FASTED VOLUNTEERS

ORAL ANTI-DIABETIC PHARMACEUTICAL FORMS AND THE PREPARATION THEREOF

FIELD OF THE INVENTION

This invention relates to novel pharmaceutical forms. More particularly, this invention relates to oral anti-diabetic pharmaceutical forms and the preparation thereof.

BACKGROUND OF THE INVENTION

Generally, in the oral administration of substances which are difficultly soluble in the digestive fluids, such as the anti-diabetic substances mentioned below, the following problems arise: in many cases the active substance can only be partly resorbed, and greatly fluctuating blood levels of the active substance may occur inter- and intra-individually. However, in oral anti-diabetic agents, the start of the activity and the duration of the activity are also of particular importance since the activity should be matched to the blood sugar levels caused by the intake of food. This is not the case with the previously available preparations of anti-diabetic agents in which the effect of the substance and physiological insulin requirements in accordance with the intake of food cannot be reliably matched to one another in terms of time. The activity of the substance often occurs too late: frequently the maximum effect is only achieved at a time at which the blood glucose values are already dropping even without medication after the intake of food. Then the activity of the substance continues even when the blood glucose has returned to its initial level (cf., Berger, in Pelzer and Froesch, Diabetische Enteropathie, Hypoglykämien, Verlag Hans Hüber, Bern-Stuttgart-Wien 1974).

Attempts have been made to synchronize the hypoglycemic activity of a sulfonyl urea with the increase in blood sugar caused by food intake by taking the sulfonyl urea at a suitable time before the meal. However, it was then found that administration of the active substance thirty minutes before the meal did not result in a satisfactory improvement in activity [cf., Sartor et al., Eur. J. Clin. Pharmacolog. 21, 403 to 408 (1982)], partly because of the longer duration of activity mentioned above. Furthermore, a specific time difference between the taking of the medicine and the taking of food can only be reliably monitored in a clinic.

There have also been attempts to solve these problems in the case of substances which are difficultly soluble in the digestive fluids by attempting to optimize the dissolution rate of the active substance difficultly soluble per se in the development of the galenic preparations. This was done, for example, by increasing the surface area of the active substance. Thus, a preparation form is described (German Pat. No. 2,348,334) in which the active substance (also a hypoglycemic substance) is present with a particle surface area of from 3 to 10 $m^2/gm$ in the presence of a wetting agent. However, this objective was also supposed to be achieved by applying the active substance in dissolved form to a substrate or carrier with the largest possible surface area and then eliminating the solvent [cf., H. Rupprecht, Acta Pharm. Technol. 26/1, pages 13 ff. (1980)].

Furthermore, attempts have been made to improve the dissolution rate by adding salt forming agents (cf., German Offenlegungsschrift No. 31 24 090.9). However, to improve the solubility and the dissolution rate, solid dispersions were also produced. They consisted of the active substance and one or more water-soluble carriers, possibly combined with surface-active substances. To prepare these dispersions, a homogeneous melt is prepared from the active substance or possibly a salt thereof and a carrier (cf., German Offenlegungsschrift No. 23 55 743). In another process, the active substance and carrier are dissolved in a common solvent, and then the solvent is eliminated. The water soluble carriers used are, inter alia, polyvinyl pyrrolidone or polyethylene glycols [cf., H. R. Merkle, Acta Pharm. Techno. 27/4, pages 193 ff. (1981), and W. L. Chiou, S. Riegelmann, J. Pharm. Sci. 60/9, 1281 ff. (1971)].

If the methods in the literature described below are used to produce preparations containing anti-diabetic substances, a better dissolution rate for the active substance, e.g., gliquidone, is scarcely obtained: the salt formation itself does not result in an increase in the dissolution rate [cf., Table 7, Example 1(c) below], and the application of active substance, e.g., gliquidone, to a carrier alone does not produce the desired result either. In corresponding tests, which will be described in more detail hereinafter, the dissolution rate was determined and, in the case of gliquidone, it was found to be no greater than the dissolution rates shown by gliquidone-containing preparations known per se.

OBJECTS OF THE INVENTION

It is an object of the invention to provide novel pharmaceutical forms.

It is also an object of the invention to provide oral anti-diabetic pharmaceutical forms.

It is a further object of the invention to provide a process for preparing said oral anti-diabetic preparations.

These and other objects of the invention will become more apparent in the discussion below.

DETAILED DESCRIPTION OF THE INVENTION

Figure 1:
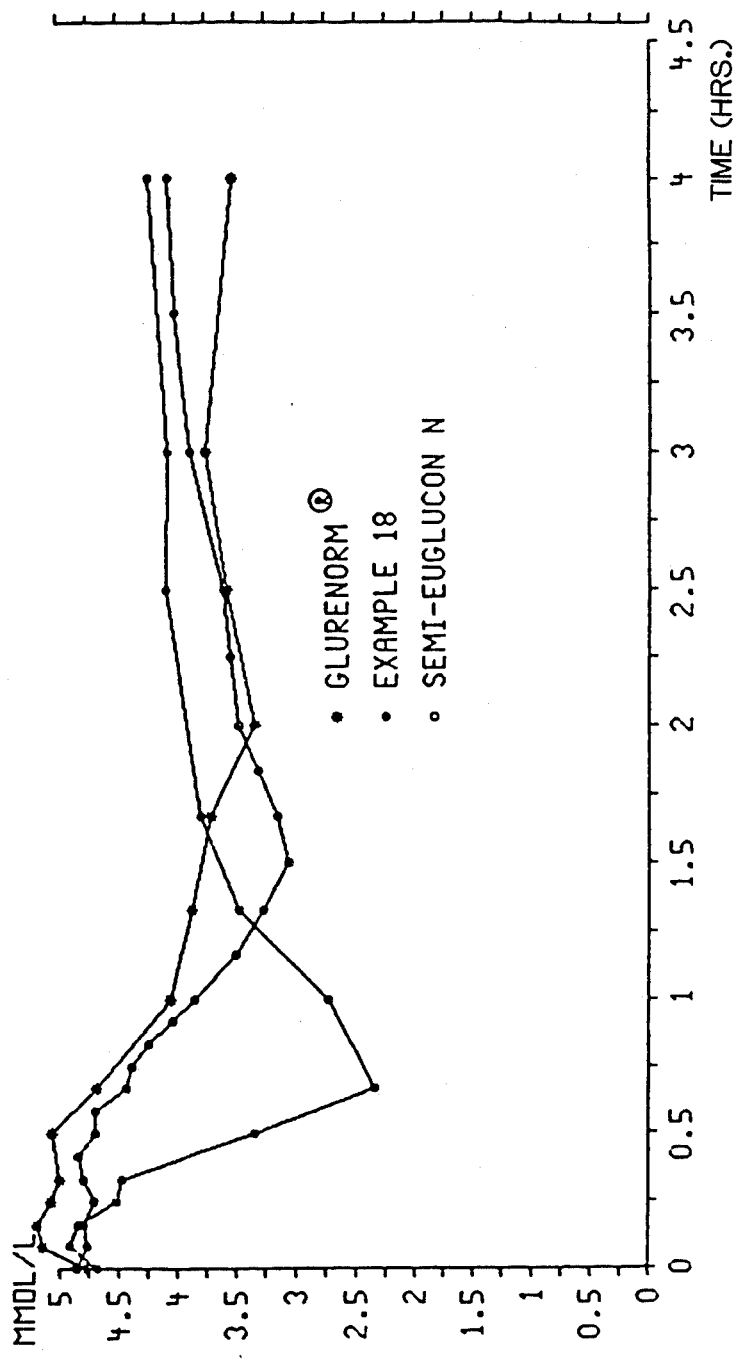

It has now been surprisingly found that preparation forms containing compounds, particularly gliquidone, with a very rapid and total release of the active substance, can be produced by converting (a) acidicly reacting active substances by means of basic adjuvants, (b) amphotericly reacting active substances by means or basic or acidic adjuvants, or (c) basicly reacting active substances by means of acidic adjuvants into a solution in the presence of one or more solubilizing substances, and applying the solution to a water-insoluble carrier and drying it, and then further processing this product, possibly with the addition of adjuvants, to form a pharmaceutical preparation. The invention also relates to the preparation forms thus obtained. In any case, however, the molar ratio of active substance to basic or acidic excipient must be selected so that there is an excess of basic or acidic excipient.

It is important that sufficient basic or acidic excipient is added to the active substance to ensure rapid and complete dissolution in vivo. This is only possible with a molar ratio of substance to basic or acidic excipient of less than 1:1.

The oral anti-diabetic agents contain as active substances sulfonyl ureas such as gliquidone or substituted phenylcarboxylic acids. Other preferred sulfonyl ureas include glibenclamide, glibornuride, glisoxepide, glipizide and gliclazide. Gliquidone is 1-cyclohexyl-3-[[p-[2-(3,4-dihydro-7-methoxy-4,4-dimethyl-1,3-dioxo-2(1H)-isoquinolyl)-ethyl]-phenyl]-sulfonyl]-urea, which has a hypoglycemic effect. However, other anti-diabetic substances which may be used are 4-[2-(aroylamino)-ethyl]-benzoic acids of the formula

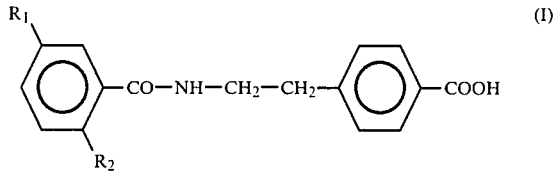

wherein $R_1$ is a halogen, preferably a chlorine atom, and $R_2$ represents an alkoxy group having from 1 to 3 carbon atoms, preferably a methoxy group, or a piperidin-1-yl or octamethyleneimino group, and also substituted 4-(aralkylaminocarbonylmethyl)-benzoic acids of the formula

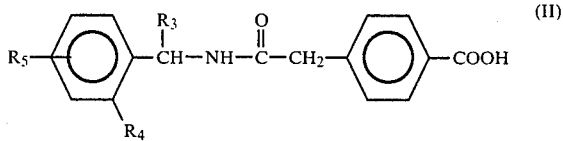

wherein $R_3$ represents an alkyl group having from 1 to 4 carbon atoms, preferably an n-propyl group, or a phenyl group, $R_4$ represents a piperidin-1-yl, pyrrolidin-1-yl, or hexamethylene imino group, and $R_5$ represents a hydrogen or halogen atom, preferably a chlorine or fluorine atom, or a methyl or methoxy group. Mixtures of these active substances may also be used.

Micronized gliquidone is contained in a commercially available preparation consisting additionally of corn starch, lactose, and magnesium stearate. This preparation containing gliquidone has already proven satisfactory as a reliable anti-diabetic agent, with the great advantage that it is not contra-indicated when there is restricted kidney function.

To dissolve 2.5 parts by weight of gliquidone, for example, in 50 parts by weight of water, 0.7 parts by weight of ethylenediamine × $1H_2O$, 3.0 parts by weight N-methyl-glucamine, or 3.5 parts by weight of diethanolamine are required. If the molar ratios which are absolutely necessary for rapid and complete dissolution of the active substance are compared, the following picture is obtained:

Gliquidone (molecular weight: 527.6): ethylenediamine × $H_2O$ (molecular weight: 78.1) as 1:1.89;

Gliquidone: N-methylglucamine (molecular weight: 195.21) as 1:3.24;

Gliquidone: diethanolamine (molecular weight: 105.14) as 1:7.03; and

Gliquidone: L-lysine (molecular weight: 146.2) as 1:4.33.

This finding cannot be explained by mere salt formation of the gliquidone with the basic excipients in question; it appears that the excess base has an additional stabilizing effect. The same phenomena also apply to the other active substances. This effect was not foreseeable even by someone skilled in the art.

Suitable basic excipients include a number of inorganic or organic bases which are physiologically harmless, that is, pharmaceutically acceptable, at least in the dosage ranges used, such as sodium hydroxide solution, potassium hydroxide solution, ammonia, tert. sodium phosphate, diethanolamine, ethylenediamine, N-methylglucamine, or L-lysine. The molar ratio of active substance to basic excipient or mixtures of excipients is preferably from about 1:1.1 to 1:10, but a greater excess of base may also be advantageous in some cases.

Suitable acidic excipients include sulfuric and phosphoric acid. The acid must be present in molar excess.

To stabilize highly concentrated solutions such as those which are clearly obtained when using a preparation according to the invention, it is necessary to add other solubilizing and/or emulsifying substances. Examples of such substances include polyvinyl pyrrolidones, polyethylene glycol 4000 or 6000, polyethoxylated sorbitan mono-oleates, sobitol, polyoxyethylene polyoxypropylene polymers, glycerol polyethylene glycoloxy stearates, and polyoxyethylene fatty alcohol ethers. Both the nature of the solubilizing substance and also the proportions used are important in determining the dissolution rate of the active substance. The ratio of active substance, e.g., gliquidone, to the total quantity of solubilizing substances is from about 1:1 to 1:10 (by weight).

The solution of the active substance, basic or acidic excipients, and solubilizing and/or emulsifying substances is prepared primarily using water or other polar solvents such as lower alcohols, e.g., ethanol, isopropanol, ketones such as acetone, or mixtures of these substances with water.

The solutions thus prepared are applied to water-insoluble carriers. Substances suitable for this purpose are preferably those which enlarge the surface area such as highly dispersed silicon dioxide, AVICEL ® (microcrystalline cellulose), basic aluminum oxide, magnesium-aluminium-trisilicates, cross-linked polyvinyl pyrrolidone, sodium carboxymethyl starch, tricalcium phosphate, calcium biphosphate, and mixtures thereof. Generally a ratio of active substance to carrier of from about 1:1 to 1:12 parts by weight is sufficient. Particularly suitable carriers are those which do not dissolve in water or some other appropriate solvent; these carriers permit easier handling both in the incorporation of the active substance and also in the further processing of the intermediate product.

By using the method of solution according to the invention instead of the melting process known from German Offenlegungsschrift No. 23 55 743, incorporated herein by reference, for incorporating the active substance, even non-fusible solubilizing substances such as the particularly advantageous polyvinyl pyrrolidone, can be distributed on the carrier in molecular dispersion together with gliquidone or the other active substances. However, in addition, water-insoluble carriers have very great advantages for galenic processes.

The solution to the problem described above is surprising for the following reasons:

The methods for incorporation of substances which are difficultly soluble in the digestive fluids, described in the literature and listed hereinafter, do not result in a significant increase in the dissolution rate of the active substance when applied to the production of preparation forms containing gliquidone, for example, nor can they improve the dissolution rate found for the commercially available preparations which contain gliquidone. The dissolution rates were determined after five and 30 minutes by the USP XX Paddle Method in 900 ml of McIlvaine Buffer, at pH 7.0, at 37° C., and at 100 rpm. For each measurement, a quantity of preparation corresponding to 40.0 mg of active substance was used, and each measurement was repeated twice. The average was calculated from the results obtained.

To determine the dissolution rate with an increase in the surface area of gliquidone, 30 parts by weight of the active substance was dissolved in 150 parts by weight of methylene chloride, and the solution was applied to 210 parts by weight of a tablet carrier. After drying, the treated tablet carrier was compressed to form tablets, and the dissolution rate of the gliquidone from these tablets was determined: 5% of the active substance dissolved after 5 minutes and 7% dissolved after 30 minutes. In the case of micronized gliquidone with no excipients, 0% dissolved after 5 and 30 minutes. When the micronized gliquidone was compressed to form tablets as in Example 1(b), 5.8% of active substance dissolved after 5 minutes and 7.2% after 30 minutes.

No better dissolution rate was obtained by forming gliquidone salts. Gliquidone was dissolved in an aqueous solution of ethylenediamine, with heating and stirring, and then further processed as described in Example 1(c). This product also yielded a quantity of only 4% of dissolved active substance after 5 minutes and 30 minutes.

Not even the use of a gliquidone-containing dispersion produced any better dissolution rates. Analogously to the method described in German Offenlegungsschrift No. 23 55 743, 1.47 parts by weight of gliquidone were dissolved in a melt consisting of 79.1 parts by weight of polyethyleneglycol 4000 and 5.0 parts by weight of polyoxyethylene-40-stearate, and then 14.43 parts by weight of potassium bicarbonate were dispersed therein. The solidified melt was rubbed through a screen with a mesh size of 1.0 mm. The measurement of the dissolution rate gave a result of 10% of active substance after 5 minutes and 7% after 30 minutes.

A further series of tests was carried out to check whether the use of gliquidone salts in the process described in German Offenlegungsschrift No. 23 55 743 leads to better dissolution rates. Again, a melt consisting of 79.1 parts by weight of polyethylene glycol 4000 and 5.0 parts by weight of polyoxyethylene-40-stearate was used, in which a saturated solution of the gliquidone salt in question was prepared. Then, 14.43 parts by weight of potassium bicarbonate was dispersed in this solution. The solidified melt was passed through a screen with a mesh size of 1.0 mm.

TABLE 1

| Gliquidone Salt containing | Maximum Active Substance (calculated as base) Soluble in Melt Consisting of PEG 4000 and Polyoxyethylene-40-stearate (%) | Quantity of Solid Solution Required for 30 mg Gliquidone for Each Dose (gm) |
| --- | --- | --- |
| Ethylenediamine | 0.65 | 4.6 |
| NH4OH | 2.40 | 1.25 |
| N—Methylglucamine | 0.54 | 5.54 |
| Piperidine | 2.15 | 1.395 |
| NaOH | 1.99 | 1.51 |

(PEG 4000 = polyethylene glycol 4000)

It is easy to see from these results that the quantity of melt required for 30 mg of gliquidone cannot be contained in a disintegrating tablet which can be swallowed. Thus, the process according to German Offenlegungsschrift No. 23 55 743 is unsuitable for gliquidone salts and also for the salts of the other active substances mentioned hereinbefore.

As can be seen from the test described above, it is not possible to achieve rapid and total dissolution of the active substances, demonstrated on gliquidone, using the known methods which are described as suitable for such purposes.

If the hypoglycemically active substances mentioned above are formulated by the processes described above, pharmaceutical compositions are obtained wherein the action of the active substance is matched to the physiological requirement of the patient for this medicament. These special pharmaceutical products ensure rapid and complete resorption of the active substance. Rapid resorption shortens the time which must elapse between taking of the medicament and taking of a meal to synchronize the hypoglycemic activity of the sulfonyl urea with the increase in blood sugar caused by food intake. Rapid and total resorption reduces intra- and inter-individual fluctuations in the blood glucose level, minimizes the dependence of resorption on the state of the gastrointestinal tract or on the nature or quantity of food taken, and thus ensures the correct metabolic pattern and consequently a correct insulin release. The disadvantages described above relating to the forms known at present are avoided by using the process according to the invention.

The essence of the invention will be investigated more closely hereinafter in a discussion of the results obtained in the tests described in the Examples. The tests were predominantly carried out with the sulfonyl urea gliquidone.

Example 1a which follows describes a preparation form consisting of gliquidone, a basic excipient, and a carrier which increases the surface area, and it shows that the dissolution rate of the gliquidone formulation according to the invention is increased significantly by comparison with the dissolution rate of gliquidone formulations known per se.

The improvements which are achieved with the addition of solubilizing substances compared with the Example 1(a) are illustrated by the findings of Examples 2 to 9, given in tabular form, which are assembled in Table 2.

Table 3 shows examples with identical amounts of different carriers with the associated dissolution rates. Since the weight ratios of gliquidone to ethylenediamine as the base to KOLLIDON ®25 as solubilizing agent were kept constant, the influence of the carrier substance on the dissolution rate can be seen.

The influence of the particular quantity of solubilizing excipient on the dissolution rate was demonstrated using the example of KOLLIDON 25 in Table 4. Table 4 also shows that the increase in the solubilizing substance in contrast to the increase in the carrier (highly dispersed silicon dioxide, cf., also Table 2) does not lead to a deterioration but to an increase in the dissolution rate.

Finally, Table 5 summarizes the influence of the particular quantity of water-insoluble carriers on the dissolution rate, by means of further examples. As this table shows, it is advantageous to avoid an excess of carriers.

Table 6 shows that it is also possible to use other alkaline toxicologically harmless excipients instead of ethylenediamine.

Figure 6:
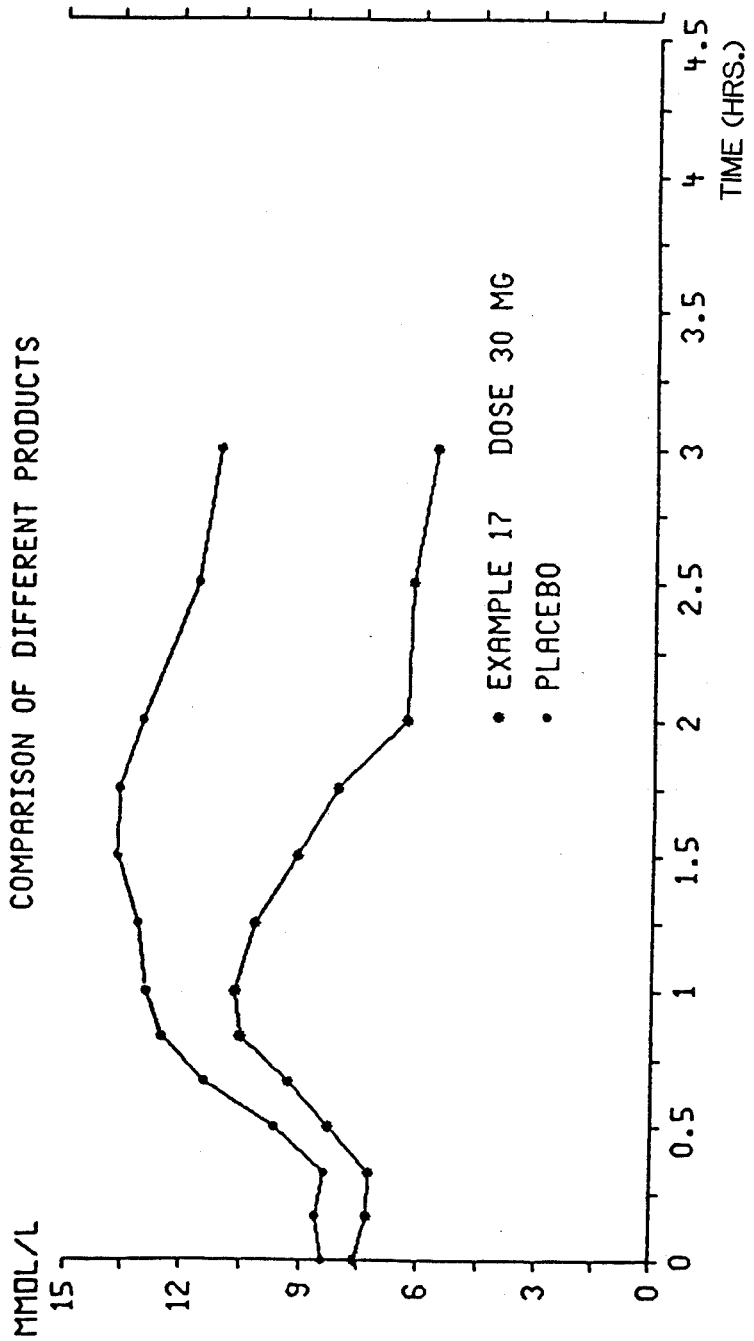
Figure 7:
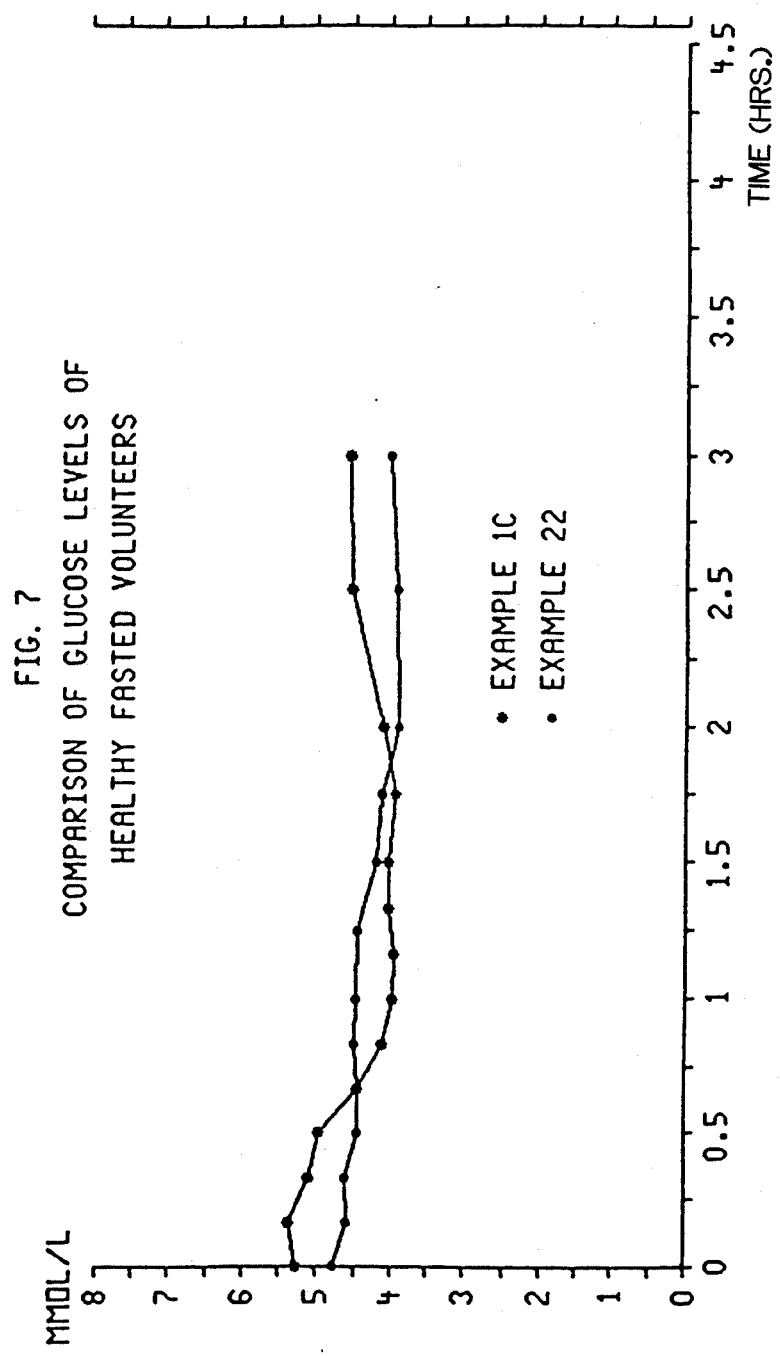

When pharmaceutical preparations are developed, optimization is carried out using in vitro methods. The release and dissolution of the active substance are determined using dissolution tests. To create conditions comparable to those which are obtained in vivo, these tests are normally carried out in an acidic medium at a pH of 1.2. If this pH is used with the forms according to the invention, no measurable release rates are obtained. In vitro dissolution tests must therefore be carried out at a pH of 7 (or above), which is due to the fact that the solubility of the active substance is no longer sufficient at pH levels below 7. It would therefore be expected that there would be only a slight release of active substance in vivo in the acidic range of the intestinal tract. The rapid and total resorption of the active substance even in the upper region of the intestinal tract is therefore surprising to one skilled in the art. It is also rather surprising in that in spite of the difference between the in vivo situation and the measurement of the dissolution rate in vitro, there is considerable agreement between in vitro and in vivo. This is shown in Examples 1(c), 17, and 22 if the results of these, which are assembled in Table 7, are compared with the corresponding human blood sugar reduction curves which are shown in FIGS. 6 and 7.

The following examples are intended to illustrate the invention and should not be construed as limiting the invention thereto. Moreover, in the examples, the following substances are employed:

AVICEL, a microcrystalline cellulose available from FMC Export Corporation Philadelphia Pa/USA;

KOLLIDON 25, a poly-N-vinylpyrrolidone(-2), available from BASF, D-6700 Ludwigshafen (West-Germany);

TWEEN ®80, a polyoxyethylene(20) sorbitan mono-oleate, available from Atlas Chemie D-4300 Essen 1, West-Germany;

PLURONIC ®F 68, a polyoxyethylene polyoxypropylene polymer, available from Wyandotte Chemicals Corp., Wyandotte Mich.;

CREMOPHOR ®RH 40, a glycerol polyethylene glycoloxy stearate, available from BASF, D-6700 Ludwigshafen, West-Germany;

AEROSIL ®, an X-ray amorphous silicon dioxide, available from Deutsche Gold- und Silberscheideanstalt, D-6000 Frankfurt, West-Germany;

MASIGEL ®, a di-magnesium-aluminium-trisilicate, available from Dr. Karl Thomae, D-7950 Biberach/Riss, West-Germany;

EXPLOTAB ®, a sodium carboxymethyl starch; available from Eastman Kodak Comp. Rochester-/USA;

KOLLIDON CL, a cross-linked insoluble polyvinyl pyrrolidone, available from BASF, D-6700 Ludwigshafen (West-Germany); and AMBERLITE ®IRP 80, a potassium salt of polymers of methacrylic acid and divinylbenzene (methacrylic acid polymer with vinylbenzene, potassium salt), available from Rohm and Haas Deutschland GmbH, Philadelphia, PA/USA.

EXAMPLES

Example 1

Composition of a gliquidone-containing powder:

| Component | Amount (parts by weight) |
| --- | --- |
| 1. Gliquidone | 5 |
| 2. Ethylenediamine × $H_2O$ | 1.9 |
| 3. AVICEL | 20 |

Preparation

The basic excipient (2) is dissolved in 100 parts by weight of water at 70° C. with stirring. The active substance (1) is added, and the mixture is stirred until the active substance is completely dissolved. The carrier (3) is suspended in this solution. The suspension is concentrated to dryness in vacuo with stirring, and the product is rubbed through a 1 mm mesh screen.

Dissolution rate found

31% gliquidone dissolved after 5 minutes;
53% gliquidone dissolved after 30 minutes.

(b) Comparison with a known gliquidone-containing preparation of the following composition:

| Component | Amount (parts by weight) |
| --- | --- |
| 1. Micronized gliquidone | 30 |
| 2. Corn Starch | 75 |
| 3. Lactose | 132 |
| 4. Magnesium stearate | 3 |

Dissolution rate found 5.8% gliquidone after 5 minutes;
7.2% gliquidone after 30 minutes.

(c) Comparison with a gliquidone-containing powder without carrier:

| Component | Amount (parts by weight) |
| --- | --- |
| (1) Gliquidone | 5 |
| (2) Ethylenediamine × $H_2O$ | 1.9 |

Preparation

The basic excipient (2) is dissolved in 100 parts by weight of water 70° C. with stirring. The active substance (1) is added, and the mixture is stirred until fully dissolved. This solution is dried in vacuo in a rotary evaporator, and the solid product is screened through a 1.00 mm mesh screen.

Dissolution rate found

4% gliquidone after 5 minutes;
4% gliquidone after 30 minutes.

Examples 2 to 9

Examples 2 to 9, which are reflected in Table 2 below, show the possibilities of influencing the dissolution rate (in percent of dissolved gliquidone) when different solubilizing substances and different quantities of one and the same carrier are used. The various compositions were prepared as follows:

The basic excipient was dissolved in water at 70° C. with stirring, and the gliquidone was added. The mixture was stirred at 70° to 80° C. until the active substance had dissolved. Then, the remaining constituents were stirred in, and the suspension was concentrated by evaporation in vacuo. The product thus formed was passed through a 1 mm mesh screen.

TABLE 2

| Example No. | Gliquidone (mg) | Ethylenediamine x H₂O as Basic Excipient (mg) | Solubilizing Excipient Quantity (mg) | Solubilizing Excipient Type | Colliodal Silica as Carrier (mg) | Dissolution Rate as percent of Active Substance Which Went Into Solution After 5 mins. | After 30 mins. |
|---|---|---|---|---|---|---|---|
| 2 | 5.0 | 1.9 | 30 | KOLLIDON 25 | 60 | 65 | 83 |
| 3 | 5.0 | 1.9 | 30 | Polyethylene glycol 6000 | 60 | 39 | 59 |
| 4 | 5.0 | 1.9 | 30 | TWEEN 80 | 60 | 34 | 40 |
| 5 | 5.0 | 1.9 | 30 | Sorbitol | 60 | 29 | 30 |
| 6 | 5.0 | 1.9 | 30 | PLURONIC F 68 | 60 | 54 | 60 |
| 7 | 5.0 | 1.9 | { 30 / 33.1 | KOLLIDON 25 / CREMOPHOR RH 40 | 30 | 79 | 89 |
| 8 | 5.0 | 1.9 | 30 | KOLLIDON 25 | 30 | 79 | 89 |
| 9 | 5.0 | 1.9 | { 30 / 33.1 | KOLLIDON 25 / CREMOPHOR RH 40 | 15 | 91 | 96 |

Examples 10 to 14

Table 3 below shows Examples 10 to 14 and also Example 2. These are examples of preparation forms containing identical amounts, that is, 60 mg, of different carriers and identical amounts of the same basic excipient, gliquidone, and the same solubilizing excipient, that is, 5 mg of gliquidone, 1.9 mg of ethylenediamine × H₂O, and 30 mg of KOLLIDON 25. Table 3 shows the effect of the particular carrier excipient on the dissolution rate. The individual compositions were prepared as described for Table 2.

TABLE 3

| Example No. | Carrier Type | Dissolution Rate in percent of Active Substance Which Went Into Solution After 5 mins. | After 30 mins. |
|---|---|---|---|
| 2 | AEROSIL | 65 | 83 |
| 10 | AVICEL | 87 | 92 |
| 11 | Basic Aluminum oxide | 56 | 64 |
| 12 | MASIGEL | 80 | 91 |
| 13 | KOLLIDON CL | 89 | 90 |
| 14 | EXPLOTAB | 95 | 95 |

Examples 15 and 16

Table 4 below contains Examples 15 and 16 together with Example 2 as a comparison. These are examples with identical quantities of gliquidone, ethylenediamine, and AEROSIL, that is, 5 mg of gliquidone, 1.9 mg of ethylenediamine × H₂O, and 60 mg of AEROSIL, but different quantities of KOLLIDON 25. The effect of the particular quantity of solubilizing excipient on dissolution rate of the active substance is shown. The individual compositions were prepared as described with reference to Table 2.

TABLE 4

| Example No. | KOLLIDON 25 as Solubilizing Substance (mg) | Dissolution Rate in percent of Active Substance Which Went Into Solution After 5 mins. | After 30 mins. |
|---|---|---|---|
| 15 | 10 | 35 | 56 |
| 2 | 30 | 65 | 83 |
| 16 | 60 | 72 | 85 |

Example 17

Example 17, together with Examples 2, 8, 9 and 10, shows the effect of the particular quantity of carrier on the dissolution rate. The values can be seen in Table 5 below. These compositions, which each comprised 5 mg of gliquidone and 1.9 mg of ethylenediamine × H₂O, were also prepared analogously to those in Table 2. Table 5 shows that increasing quantities of carrier reduces the dissolution rate.

TABLE 5

| Example No. | Solubilizing Substance Quantity (mg) | Solubilizing Substance Type | Carrier Quantity (mg) | Carrier Type | Dissolution Rate in percent of Active Substance Which Went into Solution After 5 mins. | After 30 mins. |
|---|---|---|---|---|---|---|
| 9 | { 30 / 33.1 | KOLLIDON 25 / CREMOPHOR RH 40 | 15 | AEROSIL | 91 | 96 |
| 8 | 30 | KOLLIDON 25 | 30 | AEROSIL | 79 | 89 |
| 2 | 30 | KOLLIDON 25 | 60 | AEROSIL | 65 | 83 |
| 17 | 30 | KOLLIDON 25 | 20 | AVICEL | 91 | 93 |
| 10 | 30 | KOLLIDON 25 | 60 | AVICEL | 87 | 92 |

Examples 18 to 20

The effect of different basic substances on the dissolution rate is shown by Examples 18 to 20 in Table 6. The compositions, which each comprised 5 mg of gliquidone and 27.5 mg of KOLLIDON 25, were prepared according to Table 2.

TABLE 6

| Example No. | Basic Excipient Quantity (mg) | Type | AEROSIL as Carrier (mg) | Dissolution Rate in percent of Active Substance Which Went into Solution After 5 mins. | After 30 mins. |
| --- | --- | --- | --- | --- | --- |
| 18 | 6 | N—methyl-glu-camine | 61.5 | 56 | 73 |
| 19 | 2.5 | Ethylenediamine x H₂O | 65 | 62 | 75 |
| 20 | 0.48 | Sodium hydroxide | 67.2 | 62 | 82 |

Examples 21 and 22

The preparation form in Example 21 was prepared as described in Table 2. The preparation form in Example 22 was prepared by dissolving the active substance and the solubilizing substance together in ethanol. The solution was evaporated to dryness, and the product was passed through a screen with a mesh size of 1 mm.

TABLE 7

| Example No. | Gliquidone (mg) | Ethylenediamine x H$_2$O as Basic Excipient (mg) | 30 mg of Solubilizing Agent KOLLIDON 25 | Carrier Quantity (mg) | Type | Dissolution Rate in percent of Active Substance Which Went into Solution After 5 mins. | After 30 mins. |
| --- | --- | --- | --- | --- | --- | --- | --- |
| 17 | 5 | 1.9 | Yes | 20 | AVICEL | 91 | 93 |
| 1(c) | 5 | 1.9 | No | — | — | 4 | 4 |
| 21 | 25 | 6.5 | Yes | 40 | AEROSIL | 49 | 65 |
| 22 | 25 | — | Yes | — | — | 12 | 24 |
| 1(a) | 5 | 1.9 | No | 20 | AVICEL | 31 | 53 |

As can be seen from Table 7 above, the presence of a basic excipient alone does not lead to a useful dissolution rate (cf., Example 1(c)) nor does the sole presence of a solubilizing substance (without a basic excipient and a carrier) lead to a product with a useful dissolution rate (cf., Example 22). If a carrier is added, however (cf., Example 1(a)), more than half the active substance has gone into solution after 30 minutes. If a solubilizing agent is then also added (cf., Example 17), excellent values are obtained within a very short time. This shows that the combination of gliquidone with a basic excipient and solubilizing agent in the presence of a water-insoluble carrier yields the best results in terms of rapid and fullest possible dissolution of the active substance.

The fact that the good dissolution rate of the compositions according to the invention cannot be explained solely by salt formation is also demonstrated by the following examples of tablet which were tested in vitro and partly also in vivo (cf., FIGS. 8 and 9):

Example 23

(a) Each tablet has the following composition:

| Component | Amount (mg) |
| --- | --- |
| 1. Gliquidone-L-lysine salt (equal to 30 mg of gliquidone base) | 38.31 |
| 2. EXPLOTAB | 130.0 |
| 3. AVICEL | 130.0 |
| 4. Magnesium stearate | 1.69 |
| TOTAL.: | 300.0 |

Round biconvex tablets weighing 300 mg each and measuring 10 mm in diameter are compressed from the mixture of components (1) to (4) and coated with hydroxypropyl methylcellulose to mask the flavor.

Dissolution rate

0% gliquidone after 5 minutes;
11% gliquodine after 30 minutes.

(b) Granulate of active substance/tablet has the following composition:

| Component | Amount (mg) |
| --- | --- |
| Gliquidone | 30.0 |
| L-lysine | 9.0 |
| KOLLIDON | 24.0 |
| EXPLOTAB | 48.0 |

Processing is carried out analogously to Examples 2 to 9.

The following are added for each tablet:

94.0 mg EXPLOTAB
94.0 mg microcrystalline cellulose
1.0 mg magnesium stearate

TOTAL.: 300.0 mg

The EXPLOTAB, cellulose, and magnesium stearate are added. Round biconvex tablets weighing 300 mg and measuring 10 mm in diameter are compressed from this mixture and coated with hydroxypropyl methylcellulose to mask the flavor.

Dissolution rate 46.3% gliquidone after 5 minutes;
51.2% gliquidone after 30 minutes.

(c) Granulate of active substance/tablet has the following composition:

| Component | Amount (mg) |
| --- | --- |
| Gliquidone | 30.0 |
| L-lysine | 36.0 |
| KOLLIDON 25 | 20.0 |
| PLURONIC F 68 | 24.0 |
| AVICEL | 48.0 |

Processing is carried out analogously to Examples 2 to 9.

The following are added to each tablet:

70.0 mg AVICEL
70.0 mg EXPLOTAB
2.0 mg magnesium stearate

TOTAL: 300.0 mg

Round biconvex tablets weighing 300 mg and measuring 10 mm in diameter are compressed from the mixture and coated with hydroxypropyl methylcellulose to mask the flavor.

Dissolution rate

100% gliquidone after 5 minutes.

If the salt forming agent lysine is omitted from the above composition and gliquidone is dissolved in a solution of KOLLIDON 25 and PLURONIC F 68 in water and subsequently the resulting granulate of active substance is processed in the same way to form film-coated tablets, these tablets show the following dissolution rates:

7.4% gliquidone after 5 minutes;
8.3% gliquidone after 30 minutes.

Example 24-Film-coated tablets (a) Granulate of active substance/tablet has the following composition:

| Component | Amount (mg) |
| --- | --- |
| Gliquidone | 30.0 |
| NaOH | 1.6 |
| N—Methylglucamine | 20.0 |
| KOLLIDON 25 | 20.0 |
| PLURONIC F 68 | 24.0 |
| AVICEL | 48.0 |

The granulate is prepared using a procedure analogous to that of Examples 2 to 9.

The following are added to the granulated active substance for each tablet:

| | |
| --- | --- |
| 77.0 mg | EXPLOTAB |
| 77.0 mg | AVICEL |
| 2.4 mg | magnesium stearate |
| TOTAL: 300.0 mg | | and the finished mixture is compressed to form round biconvex tablets weighing 300 mg and measuring 10 mm in diameter. These are coated with hydroxypropyl methylcellulose to mask the flavor.

Dissolution rate of gliquidone 97.6% after 5 minutes.

(b) Granulate of active substance/tablet has the following composition:

| Component | Amount (mg) |
| --- | --- |
| Gliquidone | 30.0 |
| N—Methylglucamine | 36.0 |
| KOLLICON 25 | 20.0 |
| PLURONIC F 68 | 24.0 |
| AVICEL | 48.0 |

The granulate is prepared using a procedure analogous to that of Examples 2 to 9.

The following are added to the granulate of active substance of each tablet:

| | |
| --- | --- |
| 70.0 mg | EXPLOTAB |
| 70.0 mg | AVICEL |
| 2.0 mg | magnesium stearate |
| TOTAL: 300.0 mg | | and the finished mixture is compressed to form round biconvex tablets weighing 300 mg and measuring 10 mm in diameter. These are coated with hydroxypropyl methylcellulose to mask the flavor.

Dissolution rate of gliquidone 91.1% after 5 minutes;
87.9% after 30 minutes.

Example 25-Film-coated tablets

Granulate of active substance-tablet has the following composition:

| Component | Amount (mg) |
| --- | --- |
| Gliquidone | 30.0 |
| L-lysine | 20.0 |
| NaOH | 1.6 |
| KOLLIDON 25 | 20.0 |
| PLURONIC F 68 | 24.0 |
| AVICEL | 48.0 |

The granulate of active substance is prepared analogously to Examples 2 to 9.

The following are added to the granulate of active substance for each tablet:

| | |
| --- | --- |
| 70.0 mg | EXPLOTAB |
| 70.0 mg | AVICEL |
| 2.0 mg | magnesium stearate |
| TOTAL: 300.0 mg | | and the finished mixture is compressed to form round biconvex tablets weighing 300 mg and measuring 10 mm in diameter. These are coated with a hydroxypropyl methylcellulose coating to mask the flavor.

Dissolution rate of gliquidone 92.6% after 5 minutes.

Example 26-Film-coated tablets

Each tablet has the following composition:

| Component | Amount (mg) |
| --- | --- |
| 4-[1-(2-Piperidino-phenyl)-1-butyl)-amino-carbonylmethyl]-benzoic acid | 30 |
| AMBERLITE IRP 88 | 134 |
| AVICEL | 134 |
| Magnesium stearate | 2 |
| TOTAL: | 300 |

The tablet constituents are mixed together, compressed to form round biconvex tablets weighing 300 mg and measuring 10 mm in diameter, and then coated with hydroxypropyl methylcellulose to mask the flavor.

Dissolution rate of active substance 25.6% after 5 minutes;
36.3% after 30 minutes.

Example 27-Film-coated tablets

Granulate of active substance/tablet has the following composition:

| Component | Amount (mg) |
| --- | --- |
| 4-[(1-(2-Piperidino-phenyl)-1-butyl)-amino-carbonylmethyl]-benzoic acid | 30 |

-continued

| Component | Amount (mg) |
|---|---|
| L-lysine | 36 |
| KOLLIDON 25 | 20 |
| PLURONIC F 68 | 24 |
| AVICEL | 48 |

Processing is carried out analogously to Examples 2 to 9.

The following are added to the granulate thus produced for each tablet:

> 70.5 mg AVICEL
> 70.5 mg AMBERLITE IRP 88
> 1.0 mg magnesium stearate
> TOTAL: 300.0 mg Round biconvex tablets weighing 300 mg and measuring 10 mm in diameter are compressed from this mixture and coated with hydroxypropyl methylcellulose to mask the flavor.

Dissoluton rate of active substance 46.8% after 5 minutes;
94.5% after 30 minutes.

Example 28-Film-coated tablets

Each tablet has the following composition:

| Component | Amount (mg) |
|---|---|
| 4-[N—(α-Phenyl-2-piperidino-benzyl)-amino-carbonylmethyl]-benzoic acid | 30 |
| AMBERLITE IRP 88 | 134 |
| AVICEL | 134 |
| Magnesium stearate | 2 |
| TOTAL: | 300 |

The tablet ingredients are mixed together, compressed to form round biconvex tablets weighing 300 mg and measuring 10 mm in diameter, and coated with hydroxypropyl methylcellulose to mask the flavor.

Dissolution rate of active substance 15.8% after 5 minutes;
20.9% after 30 minutes.

Example 29-Film-coated tablets

Granulate of active substance/tablet has the following composition:

| Component | Amount (mg) |
|---|---|
| 4-[N—(α-Phenyl-2-piperidino-benzyl)-amino-carbonylmethyl]-benzoic acid | 30 |
| L-lysine | 30 |
| KOLLIDON 25 | 20 |
| PLURONIC F 68 | 24 |
| AVICEL | 48 |

Processing was carried out analogously to Examples 2 to 9.

The following are added to the granulate thus prepared for each tablet:

> 73.5 mg AVICEL
> 73.5 mg AMBERLITE IRP 88
> 1.0 mg magnesium stearate
> TOTAL: 300.0 mg Round biconvex tablets weighing 300 mg and measuring 10 mm in diameter are compressed from this mixture and coated with hydroxypropyl methylcellulose to mask the flavor.

Dissolution rate of active substance 53.6% after 5 minutes;
98.2% after 30 minutes.

Example 30-Film-coated tablets

Each tablet has the following composition:

| Component | Amount (mg) |
|---|---|
| 4-[2-(5-Chloro-2-octamethyleneimino-benzoyl-amino)-ethyl]-benzoic acid | 30 |
| AMBERLITE IRP 88 | 134 |
| AVICEL | 134 |
| Magnesium stearate | 2 |
| TOTAL: | 300 |

The tablet ingredients are mixed together, compressed to form round biconvex tablets weighing 300 mg and measuring 10 mm in diameter, and then coated with hydroxypropyl methylcellulose to mask the flavor.

Dissolution rate of active substance 18.4% after 5 minutes;
27.2% after 30 minutes.

Example 31-Film-coated tablets

Granulate of active substance/tablet has the following composition:

| Component | Amount (mg) |
|---|---|
| 4-[2-(5-Chloro-2-octamethyleneimino-benzoyl-amino)-ethyl]-benzoic acid | 30 |
| L-lysine | 36 |
| KOLLIDON 25 | 20 |
| PLURONIC F 68 | 24 |
| AVICEL | 48 |

Processing is carried out analogously to Examples 2 to 9.

The following are added to the granulate thus prepared for each tablet:

> 70.5 mg AVICEL
> 70.5 mg AMBERLITE IRP 88
> 1.0 mg magnesium stearate
> TOTAL: 300.0 mg Round biconvex tablets weighing 300 mg and measuring 10 mm in diameter are compressed from this mixture and coated with hydroxypropyl methylcellulose to mask the flavor.

Dissolution rate of active substance 98.2% after 5 minutes;
98.7% after 30 minutes.

The following are additional examples of the production of pharmaceutical preparation forms:

Example 32

Capsules

A quantity of granulate from Example 9 corresponding to 15 mg of gliquidone is mixed with a corresponding quantity of corn starch and magnesium stearate and then packed into size 2 hard gelatine capsules.

Example 33

Capsules

A quantity of granulate from Example 13 corresponding to 15 mg of gliquidone is mixed with a corresponding quantity of corn starch and magnesium stearate and packed into size 1 hard gelatine capsules.

Example 34

Film-coated tablets

A quantity of granulate from Example 13 corresponding to 30 mg of gliquidone is mixed with AVICEL and magnesium stearate and compressed to form oval cores measuring 16×8 mm in diameter and weighing 700 mg in a tablet-making machine. The cores are then coated in a coating pan with a flavor-masking coating of hydroxypropyl methylcellulose corresponding to 14 mg of dry substance.

Example 35

Film-coated tablets

A quantity of granulate from Example 17 corresponding to 30 mg of gliquidone is combined with an auxiliary granulate of lactose, corn starch, and AEROSIL, and after the addition of magnesium stearate, the mixture is compressed to form round biconvex cores measuring 11 mm in diameter and weighing 400 mg in a tablet-making machined. These cores are then coated in a coating pan with a flavor-masking coating of hydroxypropyl methylcellulose corresponding to 8 mg of dry substance.

Example 36

Quantities of 3.5 mg of glibenclamide, 4.2 mg of N-methylglucamine, 19.25 mg of KOLLIDON 25, and 14.0 mg of AVICEL are processed as described for Table 2. A quantity of this preparation corresponding to 42 mg of glibenclamide is used, according to the particular requirements.

Dissolution rate found

Glibenclamide-97.9% after 5 minutes;
Glibenclamide-93.6% after 30 minutes.

By contrast, the corresponding commercially available product EUGLUCON ®N showed the following results in the dissolution test (12 tablets/900 ml):

Glibenclamide-16.8% after 5 minutes;
Glibenclamide-13.8% after 30 minutes.

If only 21 mg of glibenclamide are used instead of 42 mg of glibenclamide, the following dissolution rates are obtained:

(a) with the above preparation:
Glibenclamide-95.6% after 5 minutes;
Glibenclamide-98.8% after 30 minutes.
(b) with EUGLUCON N (=6 tablets/900 ml):
Glibenclamide-29.4% after 5 minutes;
Glibenclamide-27.3% after 30 minutes.

The preparation of glibenclamide according to the invention is far superior to the commercially available EUGLUCON N in its dissolution rate, as is shown predominantly by the comparison carried out with 42 mg of glibenclamide/900 mg of liquid.

Example 37

Each tablet has the following composition:

| Component | Amount (mg) |
| --- | --- |
| 4-[(1-(2-Piperidino-phenyl)-1-butyl)-aminocarbonylmethyl]-benzoic acid | 30.0 |
| PLURONIC F 68 | 24.0 |
| KOLLIDON 25 | 20.0 |
| $H_2SO_4$ | 7.5 |
| SUBTOTAL: | 81.5 |

Preparation

The active substance is dissolved in a mixture of ethanol and 1N sulfuric acid. PLURONIC F 68 and KOLLIDON 25 are then dissolved in this solution. The solution is concentrated by evaporation, and the residue is passed through a screen with a mesh size of 1 mm and mixed with the following remaining tablet constituents:

| Component | Amount (mg) |
| --- | --- |
| AMBERLITE IRP 88 | 108.5 |
| AVICEL | 108.5 |
| Magnesium stearate | 1.5 |
| TOTAL: | 300.0 |

Round biconvex tablets weighing 300 mg are compressed from this mixture and then coated with hydroxypropyl methylcellulose to mask the flavor.

The results and explanations of human testing set forth below and in FIGS. 1 to 10 show that the pharmaceutical forms prepared according to the invention have the advantages mentioned hereinbefore:

FIG. 1 shows the path of the blood sugar level after the administration of a preparation according to Example 1(b) (commercial gliquidone preparations), a preparation according to the invention, and a preparation containing glibenclamide, with the brand name EUGLUCON N or SEMI-EUGLUCON ®N. On the basis of the human testing described in German Pat. No. 2,348,334 and the data on EUGLUCON N in the literature, it must be assumed that this preparation is produced analogously to the recipe in the Patent specification. It is found that the start of the activity occurs much faster when using the preparation according to the invention and stops in a shorter time than with the other two preparations. (With the known and highly effective glibenclamide, the maximum activity is not achieved until about 1.5 hours after administration, and the activity does not end until more than four hours later.)

Figure 2:
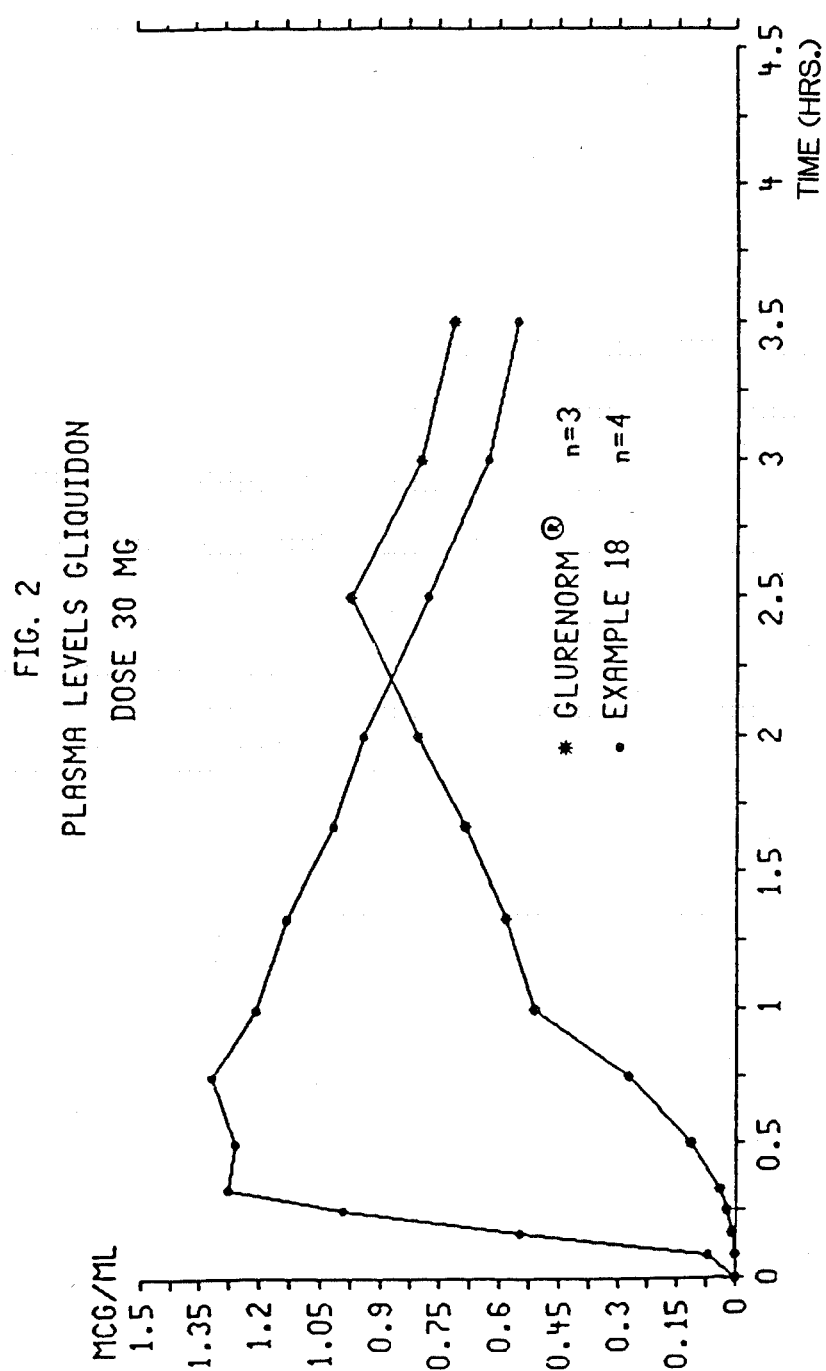

FIG. 2 shows the path of the gliquidone plasma levels after the administration of a preparation according to Example 1(b) (commercial gliquidone preparation) and a preparation produced according to the invention. It is apparent that the faster onset of the activity is clearly caused by the faster resorption.

Figure 3:
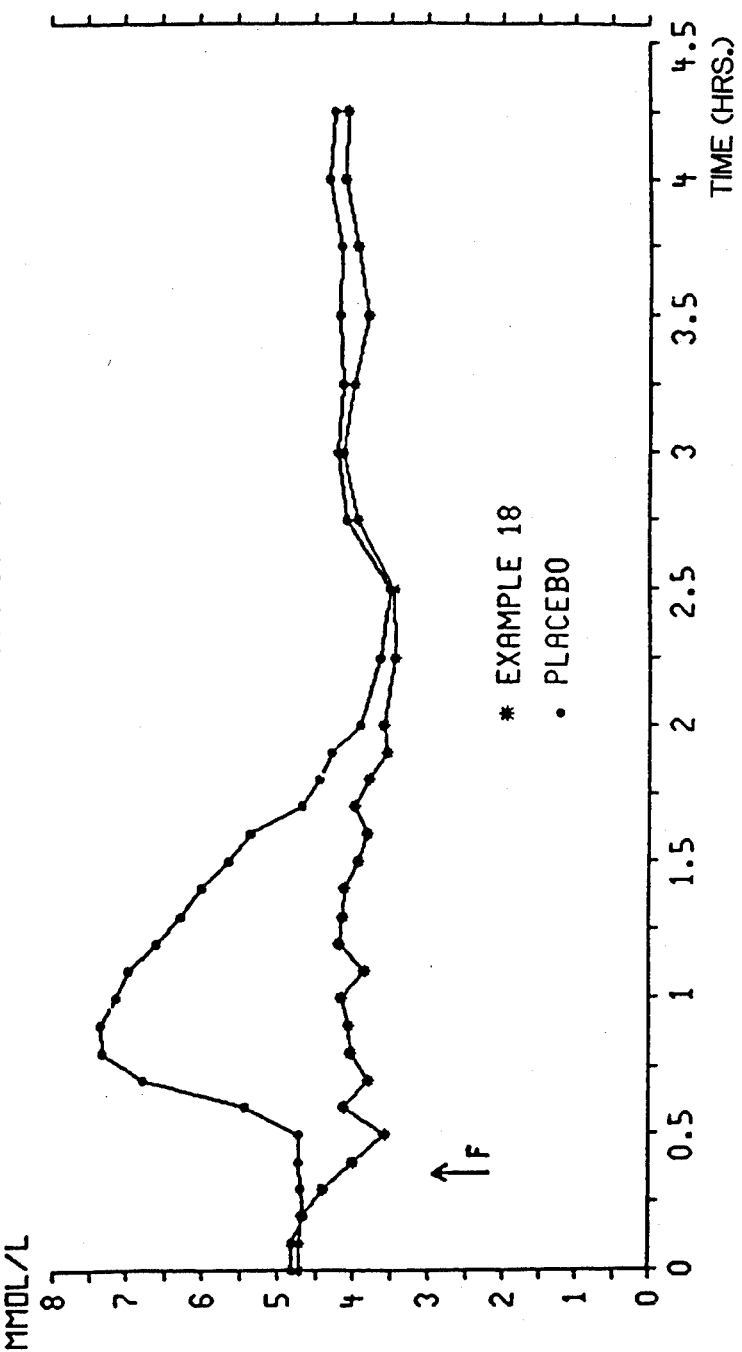
Figure 4:
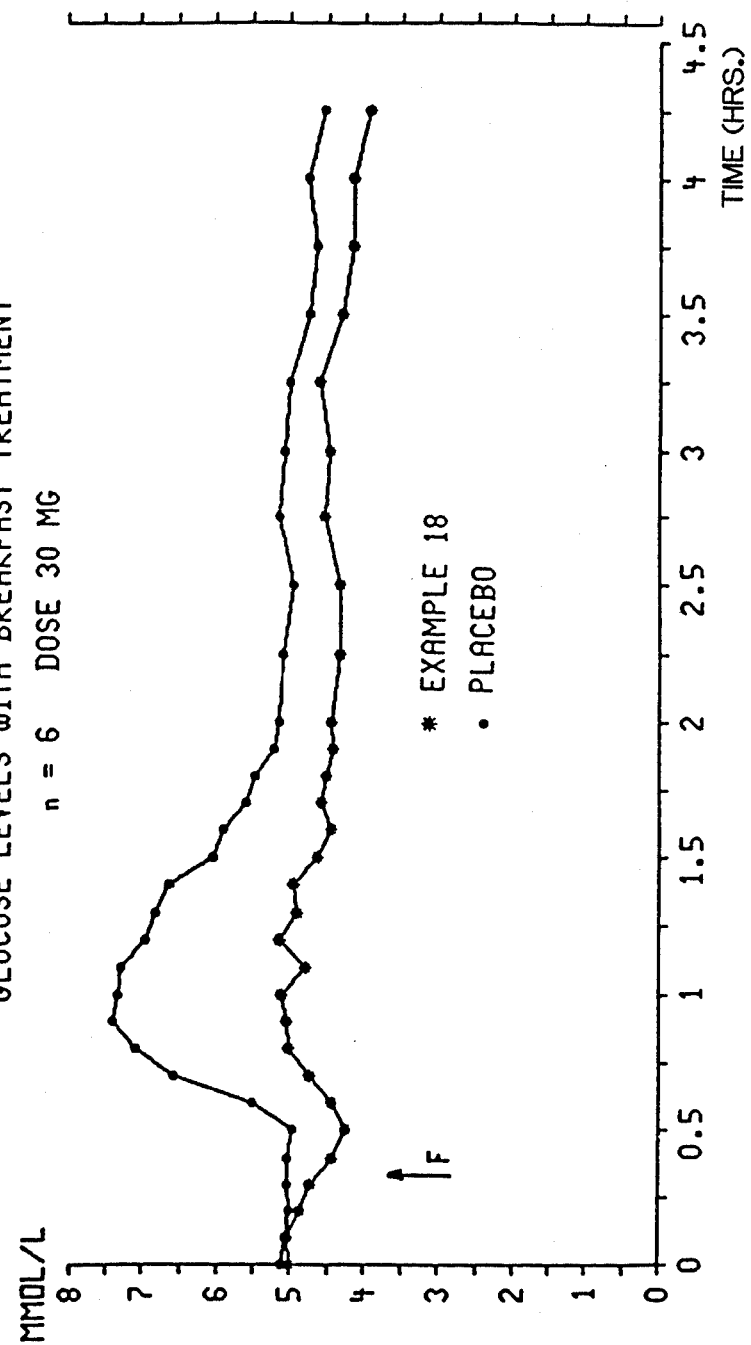

FIG. 3 illustrates the path of the blood sugar levels after the administration of a placebo and a preparation according to the invention in a cross-over test on healthy volunteers with an intake of 50 gm of carbohydrate in the form of a mixture of glucose, disaccharides, and oligosaccharides (DEXTRO OGT®). FIG. 4 again shows the path of the blood sugar levels, but upon consumption of a standard breakfast. A standard breakfast is made up of two cups of black tea each containing 10 gm of sugar, two half rolls with 5 gm of butter each, and 7 gm of honey. FIGS. 3 and 4 show that the rise in the blood sugar level flattens out almost completely after the meal of carbohydrate. This means that the start of the activity and the course of the activity are optimally adapted to the course of the carbohydrate levels on the intake of food.

Figure 5:
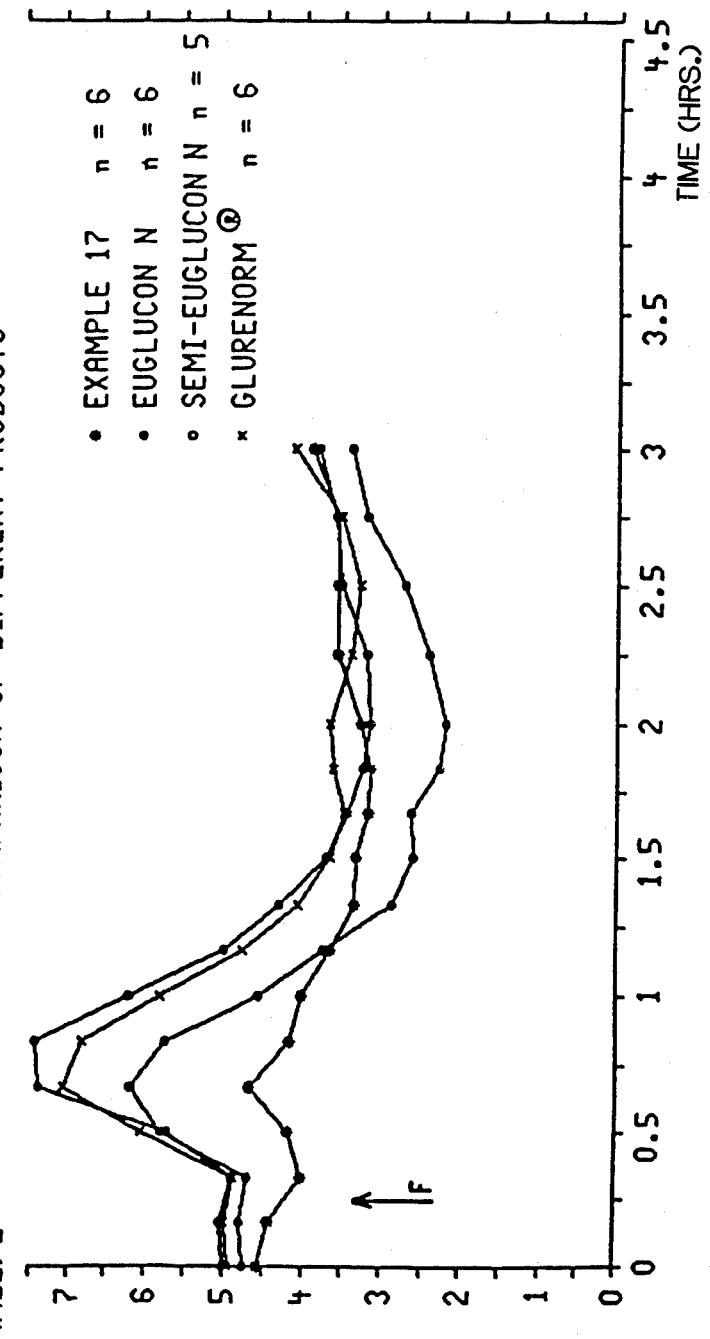

FIG. 5 shows the course of the blood sugar level upon consumption of a standard breakfast after administration of a preparation according to Example 17 (preparation according to the invention), Example 1(b) (commercial gliquidone preparation), and two preparations containing glibenclamide (EUGLUCON N and SEMI-EUGLUCON), breakfast being taken 15 minutes after the administration of the drug. It is found with one of the preparations that the higher dosage does indeed reduce the increase in the blood sugar level but then causes a sharp fall in blood sugar after some time. This means that even by increasing the dosage the desired effect cannot be achieved without risk. In contrast to the commercial forms, with the preparation according to the invention the rise in the blood sugar level after the taking of breakfast can be almost completely absorbed without leading to excessively low blood levels.

FIG. 6 shows the path of the blood sugar levels in a type 2 diabetic after the administration of a placebo and a preparation according to the invention, breakfast being taken 10 minutes after the administration of the drug. As can be seen from these curves, the administration of the preparation according to the invention adapts the rise in blood sugar, in terms of its level and duration, to physiological conditions which occur in people with healthy metabolism (cf., Placebo curve, FIG. 4).

FIG. 7 shows, as already described on pages 14, 26, and 27, the agreement between the in vitro results and in vivo results.

However, measurement of the peripheral insulin levels also illustrates the advantageous course of effect of the preparations according to the invention.

By measuring the peripheral insulin levels during the consumption of glucose or breakfast, the quantity of insulin released was calculated. The preparation according to the invention does not cause more insulin to be released as a whole than does glucose on its own. Calculation of the incremental areas clearly shows the early stimulation of the group treated with the preparation according to the invention. In the time from 0 to 42 minutes, twice the amount of insulin is increased as compared with the placebo group (Table 8). For the phase from 42 to 300 minutes, the differences are small and do not reach a significant level in any case. The powerful effect on blood sugar can therefore be explained by an increase in early insulin secretion. There is no therapeutically undesirable excessively long high-lasting stimulation of insulin secretion.

TABLE 8

INCREMENTAL AREAS UNDER THE PLASMA INSULIN CURVE [AVERAGE + SEM (µE MIN/ML)]

|  |  | 0–42 minutes | 42–300 minutes |
|---|---|---|---|
| Placebo | Breakfast n = 6 | 722 ± 171 | 6260 ± 1346 |

TABLE 8-continued

INCREMENTAL AREAS UNDER THE PLASMA INSULIN CURVE [AVERAGE + SEM (µE MIN/ML)]

|  |  | 0–42 minutes | 42–300 minutes |
|---|---|---|---|
|  | Glucose n = 6 | 558 ± 156 | 4597 ± 900 |
| Preparation According to Invention | Breakfast n = 6 | 1384 ± 298 | 5196 ± 873 |
|  | Glucose n = 6 | 1468 ± 312 | 5420 ± 810 |

The effect on insulin secretion in seven diabetics, of whom two were stabilized by diet alone, two used EU-GLUCON or SEMI-EUGLUCON N (preparations containing glibenclamide), and three used a preparation according to the invention containing gliquidone, showed the superiority of the new preparation according to the invention compared with the standard medication (Table 9 below) tested in a cross-over test. In relation to basal insulin secretion, the new form demonstrated significantly greater stimulation of the early phase of insulin secretion (0 to 40 minutes) than the corresponding standard medication. In the subsequent period (40 to 300 minutes) there was a trend toward a reduction in insulin levels. This shows that the stimulation of only the earlier insulin secretion in accordance with the objective of the therapy is achieved not only with those of healthy metabolism but also in the target group, namely, type 2 diabetics.

TABLE 9

INCREMENTAL AREAS UNDER THE PLASMA INSULIN CURVE OF 7 TYPE 2 DIABETICS DURING A STANDARD BREAKFAST [AVERAGE ± SEM (PERCENT OF BASAL AREA)]

|  | 0–40 minutes | 40–300 minutes |
|---|---|---|
| Standard medication | 190 ± 14 | 424 ± 53 |
| Preparation According to The Invention | 318 ± 43 | 378 ± 53 |

The findings mentioned above show that the medical objectives:

(a) avoiding a non-physiological rise in blood sugar after the intake of food;

(b) avoiding a massive drop in blood sugar some hours after food intake; and (c) early, brief release of insulin during the intake of food, are achieved with the gliquidone-containing preparations according to the invention.

Figure 8:
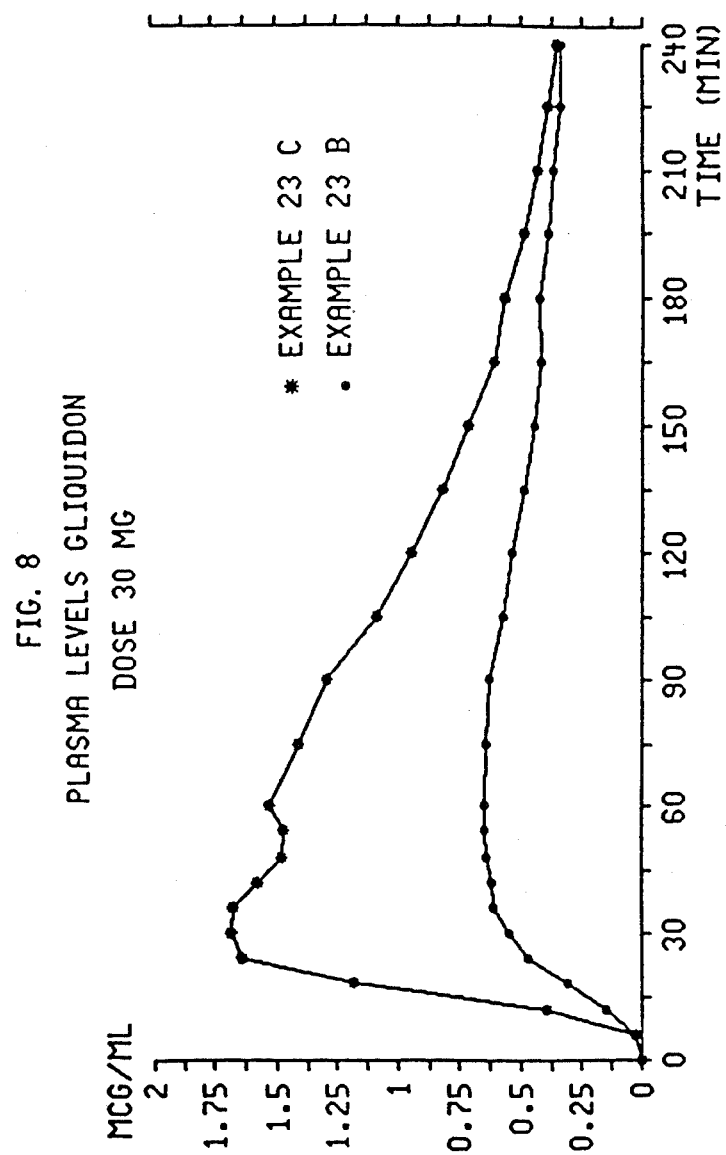

FIG. 8 shows the course of the plasma levels of gliquidone after the administration of two preparations containing L-lysine as the basic excipient. It is clear that the composition analogous to Example 23(b) results in only relatively low plasma levels, whereas excellent results are obtained on administration of preparations according to Example 23(c). This proves that a significant excess of basic active substance is necessary for an adequate in vivo release of the active substance, i.e., the positive effect is not only due to salt formation.

Figure 9:
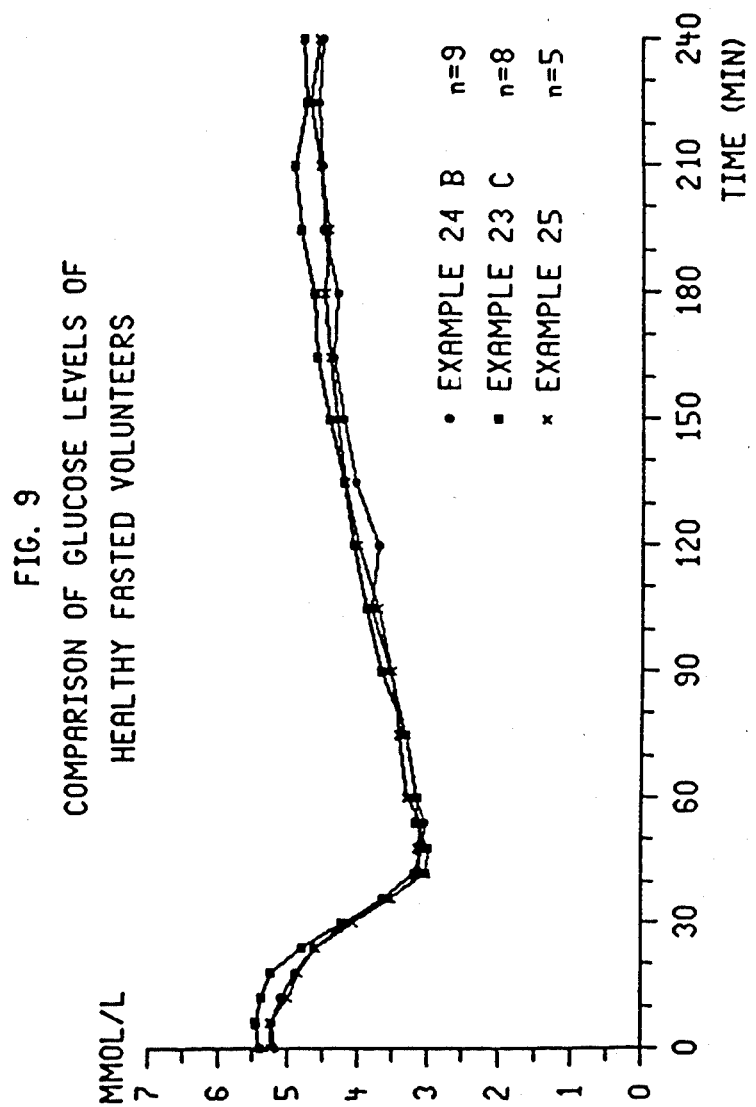

FIG. 9 shows that the requirements regarding an optimal pharmaceutical preparation for diabetics mentioned hereinbefore can be achieved with various compositions (Examples 23(c), 24(b), 25). However, the quantity of excipients must be optimized individually in each separate case.

Experiments were also carried out to find out whether faster acting forms are possible with the active substance glibenclamide, which does not have an ideal profile for the blood sugar curve in its commercial form of EUGLUCON N. For this purpose, the commercial form and a composition analogous to Example 36 were compared on eight and six healthy volunteers, respectively.

Figure 10:
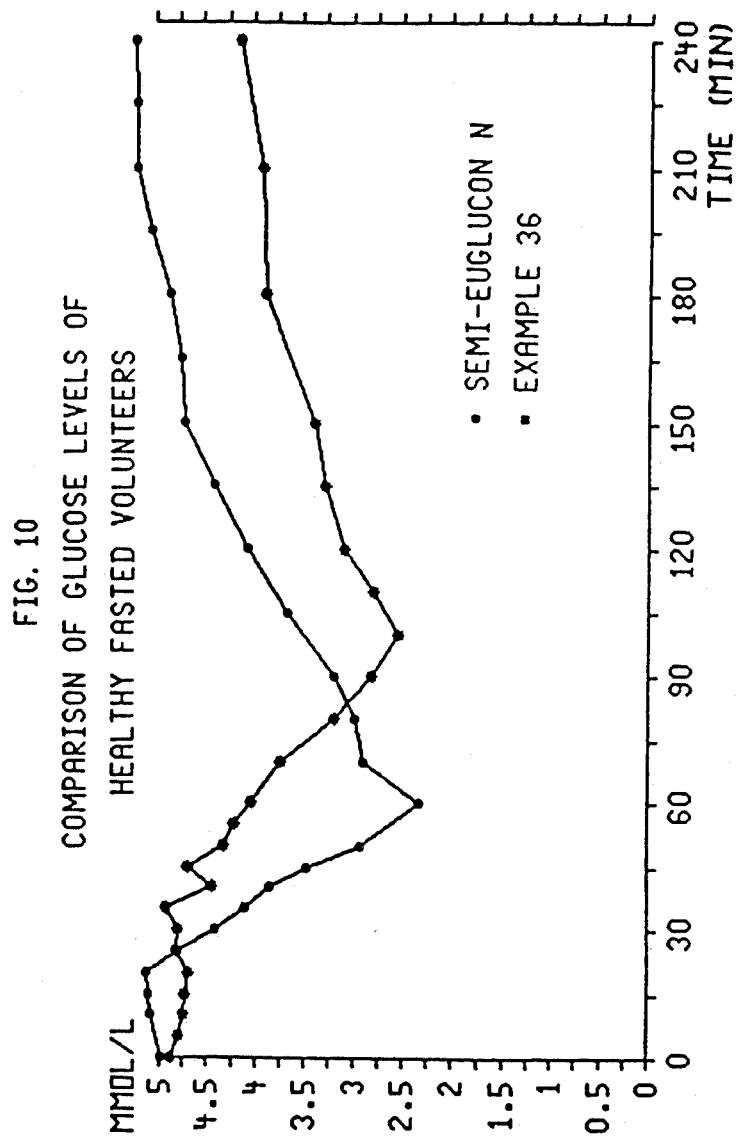

FIG. 10 shows blood sugar patterns in a test subject who took both forms on different days. It is apparent that a faster onset of activity and a shorter duration of activity can also be achieved for glibenclamide.

The methods of measurement used were as follows:

Determining the Blood Glucose

The blood sugar was measured in whole venous blood. Fifty microliters of blood were freed from protein with 500 µl of 0.32M perchloric acid. After centrifuging, the glucose in the supernatant was measured by the hexokinase method using an automatic substrate.

Determining the Plasma Insulin

Insulin was determined from venous plasma by radioimmunology using the active charcoal method.

Six hundred microliters of whole blood were mixed with 50 µl of Trasylol-EDTA-heparin mixture (5 ampules of Trasylol/Bayer, 1.2 gm of EDTA+ethylenediaminetetraacetate, 150 mg heparin, and 75 ml of physiological saline solution), then the mixture was centrifuged, and immunoreactive insulin in the supernatant was measured. One hundred microliters of plasma were dissolved with 100 µl of $^{125}$I-pig insulin (Novo), in a phosphate buffer according to Soerensen, and 250 µl of anti-pig insulin-guinea pig serum M 8309 (Novo) was incubated at 4° C. for 23 hours. Then, the free insulin was separated from the bound insulin using active charcoal (Norit/Serva) and DEXTRAN T 70 (Pharmacia), filtered, and measured in a gamma counter.

Determining the Plasma Levels

The plasma levels were determined by HPLC. The measurement was carried out in a semi-automatic HPLC machine with column switching (for apparatus, see Journ. of Chromatography, 222 (1981), pages 13 to 22). The measurement was made using an external standard. In the analytical column 5µ of reversed phase material (HYPERSIL ODS ®) was used; CORASIL C 18 ® was used for the preliminary column, in an amount of 37 to 50µ. The mobile phase used was a mixture of methanol, water, and piperidone (600:500:1). The substance was measured by fluorimetry (excitation wavelengths 318 nm, emmission wavelengths 412 nm).

Human Testing

Blood samples were taken through long-turn catheters with heparinized disposable syringes. After a preliminary period of 15 minutes in which the course of the blood sugar level and of the insulin level without any medicament was measured, the galenic preparation was administered in the form of a granulate or in tablet form in the appropriate dosage with 70 ml of water.

The anti-diabetically active substances useful according to the invention are administered orally, optionally in combination with other active ingredients, in known manner. The daily dose for adults is from about 5 to 150 mg (from about 0.07 to 2 mg/kg of body weight), preferably from about 10 to 120 mg (from about 0.18 to 1.6 mg/kg of body weight), generally administered in the form of several, preferably from 2 to 4, individual doses to achieve the desired results. Dependent upon the type and body weight of the patient to be treated, on the type and severity of the disease, on the type of preparation and on the route of administration as well as on the period or interval over which the administration takes place, it may, however, be necessary to deviate from the above dosages. Thus it may be sufficient in some cases to administer more or less than the above-mentioned amounts of active ingredient. The optimum dosage and route of adminstration of the active ingredients which are necessary in each case can easily be determined by one skilled in the art.

The compositions prepared according to the invention can be further processed to produce pharmaceutical compositions useful for administration according to the invention. For example, the compositions can be admixed with conventional pharmaceutical excipients to form tablets, coated tablets, capsules, solutions and the like. Such conventional excipients include for example, microcrystalline cellulose, potassium salt of polymers of methycrylic acid and divinylbenzene, magnesium stearate, lactose corn starch, polyvinyl pyrrolidone, gelatine, and the like.

The preceding specific embodiments are illustrative of the practice of the invention. It is to be understood, however, that other expedients known to those skilled in the art or disclosed herein, may be employed without departing from the spirit of the invention or the scope of the appended claims.

We claim:

1. The method of preparing an oral antidiabetic pharmaceutical composition containing an antidiabetic sulfonyl urea as the active ingredient, which comprises dissolving or emulsifying
   (a) an acid antidiabetic sulfonyl urea with a basic excipient, or
   (b) an amphoteric antidiabetic sulfonyl urea with a basic or acid excipient, or
   (c) a basic antidiabetic sulfonyl urea with an acid excipient in an inert polar solvent in the presence of at least one solubilizing or emulsifying substance, where the molar ratio of sulfonyl urea to basic or acid excipient is less than 1:1 and the ratio of sulfonyl urea to the total of solubilizing or emulsifying substance is from about 1:0.5 to 1:10 parts by weight, applying the resulting solution or emulsion to the surface of at least one water-insoluble carrier, where the ratio of sulfonyl urea to the total of water-insoluble carrier is from 1:1 to 1:12 parts by weight, and drying the thus treated water-insoluble carrier.

2. The method of claim 1, where said sulfonyl urea is gliquidone, glibenclamid, glibornuride, glisoxepide, glipizide or gliclazide.

3. The method of claim 1, where said basic excipient is sodium hydroxide, potassium hydroxide, ammonia, tert.sodium phosphate, diethanoamine, ethylenediamine, N-methyl-glucamine or L-lysine, and said acid excipient is sulfuric acid or phosphoric acid.

4. The method of claim 1, where said sulfonyl urea is gliquidone.

5. The method of claim 1, where the molar ratio of sulfonyl urea to basic or acid excipient is 1:1.1 to 1:10.

6. The method of claim 1, wherein the water-insoluble carrier is selected from the group consisting of highly dispersed silicon dioxide, microcrystalline cellulose, basic aluminum oxide, magnesium-aluminumtrisilicate, cross-linked polyvinylpyrrolidone, sodium carboxymethyl starch, tricalcium phosphate, calcium biphosphate and mixtures thereof, and the solubilizing or emulsifying substance is selected from the group consisting of polyvinylpyrrolidone, polyethylene glycol, polyethoxylated sorbitan monooleate, sorbitol, polyoxyethylene polyoxypropylene polymer, polyoxyethylene fatty alcohol ether, glycerol polyethylene glycoloxy stearate, and mixtures thereof.

7. The method of claim 1, wherein the solubilizing substance is polyvinylpyrrolidone, polyoxyethylene polyoxypropylene polymer or a mixture thereof.

8. The method claim 1, wherein the basic excipient is selected from the group consisting of a pharmacologically acceptable inorganic and organic base.

9. The method of claim 1, wherein the dry treated water-insoluble carrier is combined with a conventional pharmaceutical excipient to produce the desired oral antidiabetic pharmaceutical composition.

10. An oral antidiabetic pharmaceutical composition consisting essentially of a conventional pharmaceutical excipient and a dry water-insoluble carrier having applied to the surface thereof the evaporation residue of a solution or emulsion of an effective antidiabetic amount of an acid, amphoteric or basic antidiabetic sulfonyl urea, a basic or acid excipient, and at least one solubilizing or emulsifying substance in an inert polar solvent, where the molar ratio of sulfonyl urea to basic or acid excipient is less than 1:1, the ratio of sulfonyl urea to the total of solubilizing or emulsifying substance is from 1:0.5 to 1:10 by weight, and the ratio of sulfonyl urea to the total of water-insoluble carrier is from 1:1 to 1:12 parts by weight.

11. A composition of claim 10, where said sulfonyl urea is gliquidone, glibenclamid, gliboruride, glisoxepide, glipizide or gliclazide.

12. A composition of claim 10, where said sulfonyl urea is gliquidone.

13. A composition of claim 10, where said basic excipient is sodium hydroxide, potassium hydroxide, ammonia, tert.sodium phosphate, diethanolamine, ethylenediamine, N-methyl-glucamine or L-lysine, and said acid excipient is sulfuric acid or phosphoric acid.

14. A composition of claim 10, where the molar ratio of sulfonyl urea to basic or acid excipient is from 1:1.1 to 1:10.

15. A composition of claim 10, wherein the basic excipient is selected from the group consisting of a pharmacologically acceptable inorganic and organic base, the acid excipient is sulfuric acid, the water-insoluble carrier is selected from the group consisting of highly dispersed silicon dioxide, microcrystalline cellulose, basic aluminum oxide, magnesium-aluminum-trisilicate, cross-linked polyvinylpyrrolidone, sodium carboxymethyl starch, tricalcium phosphate, calcium biphosphate and mixtures thereof, and the solubilizing or emulsifying substance is selected from the group consisting of polyvinylpyrrolidone, polyethylene glycol, polyethoxylated sorbitan monooleate, sorbitol, polyoxyethylene polyoxypropylene polymer, glycerol polyethylene glycoloxy stearate and mixtures thereof.

16. A method for the treatment of diabetes in a warm-blooded host in need of such treatment, which comprises orally administering to said warm-blooded host a composition of claim 10.

* * * * *